United States Patent [19]

Callinan et al.

[11] Patent Number: 5,540,652
[45] Date of Patent: Jul. 30, 1996

[54] ORTHOPEDIC CAST COMPOSED OF AN ALKOXYSILANE TERMINATED RESIN

[75] Inventors: Andrew Callinan, Robbinsdale; Matthew T. Scholz, Woodbury, both of Minn.

[73] Assignee: Minnesota Mining and Manufacturing Company, St. Paul, Minn.

[21] Appl. No.: 386,017

[22] Filed: Feb. 9, 1995

Related U.S. Application Data

[62] Division of Ser. No. 48,656, Apr. 16, 1993, Pat. No. 5,423,785.

[51] Int. Cl.$^6$ .............. A61F 5/04; B32B 27/04; B32B 27/40; B32B 31/24
[52] U.S. Cl. .............. 602/1; 427/341; 428/251; 428/252; 428/253; 428/272; 428/273; 428/288; 428/290; 428/423.1; 428/425.6; 428/542.8
[58] Field of Search .............. 602/1, 8; 525/403, 525/404, 408; 528/26, 28; 428/251, 252, 253, 272, 273, 288, 290, 423.1, 425.6; 427/341

[56] References Cited

U.S. PATENT DOCUMENTS

| | | | |
|---|---|---|---|
| 4,180,642 | 12/1979 | Takago | 528/32 |
| 4,411,262 | 10/1983 | von Bonin et al. | |
| 4,442,833 | 4/1984 | Dahlen et al. | 602/8 |
| 4,502,479 | 3/1985 | Garwood et al. | |
| 4,562,237 | 12/1985 | Okuno et al. | 528/17 |
| 4,570,622 | 2/1986 | von Bonin et al. | |
| 4,609,578 | 9/1986 | Reed | 428/76 |
| 4,619,578 | 10/1986 | Routledge | 414/498 |
| 4,657,986 | 4/1987 | Isayoma et al. | 525/407 |
| 4,667,661 | 5/1987 | Scholz et al. | |
| 4,668,563 | 5/1987 | Buese et al. | 428/230 |
| 4,774,937 | 10/1988 | Scholz et al. | |
| 4,793,330 | 12/1988 | Honeycutt et al. | 602/8 |
| 4,841,958 | 6/1989 | Ernsfeld et al. | |
| 4,871,845 | 10/1989 | Buckanin | 544/87 |
| 4,889,903 | 12/1989 | Baghdachi | 528/17 |
| 4,940,047 | 7/1990 | Richter et al. | |
| 4,954,598 | 9/1990 | Baghdachi et al. | 528/22 |
| 5,005,566 | 4/1991 | Klintworth, Jr. | |
| 5,047,293 | 9/1991 | Jansen et al. | 428/423.1 |
| 5,052,380 | 10/1991 | Polta | |
| 5,090,405 | 2/1992 | Jansen et al. | 602/8 |

FOREIGN PATENT DOCUMENTS

PCT/US94/01717  7/1984  WIPO.

*Primary Examiner*—James C. Cannon
*Attorney, Agent, or Firm*—Gary L. Griswold; Walter N. Kirn; F. Andrew Ubel

[57] ABSTRACT

The present invention provides a water-curable resin composition for use in an orthopedic cast composed of a water-reactive alkoxysilane terminated resin, having at least one hydrolyzable group per molecule. The resin composition has a viscosity of no greater than about 500 Pa-s under ambient conditions and contains less than about 1 wt-% of a solvent, based on the total weight of the resin composition.

19 Claims, 1 Drawing Sheet

ORTHOPEDIC CAST COMPOSED OF AN ALKOXYSILANE TERMINATED RESIN

This is a division of application Ser. No. 08/048,656 filed Apr. 16, 1993 and now U.S. Pat. No. 5,423,785.

FIELD OF THE INVENTION

The present invention relates to orthopedic support materials made of a substrate impregnated with a water-curable resin composition. The invention also relates to methods of making the support materials, methods of making casts from the support materials, and the resulting products.

BACKGROUND OF THE INVENTION

While the methods, compositions, and materials presented herein can be used in a variety of applications, they are well adapted for use with respect to orthopedic support materials, such as casting tapes and splints. Therefore, as background, characterizations of technology relating to orthopedic casting tapes and problems overcome by the present invention are provided.

Orthopedic casting tapes have been produced using curable resins coated or impregnated onto a substrate. Typically, the casting tape is stored as a roll in a water-impermeable storage pouch until needed for use. When needed, the roll of tape is removed from the pouch and contacted with water. Generally, the tape includes a resin therein that is water-curable. Thus, shortly after the tape is dipped in water, the resin will begin to cure and the tape harden. A medical practitioner applies the casting tape to a patient immediately after it has been soaked with water. Generally, resin materials are chosen that begin to cure immediately after being dipped in water, and that will set, i.e., harden sufficiently to resist passive motion in a joint, e.g., a wrist or ankle, in about 3–5 minutes, and to be weight bearing within about 30 minutes.

Typical resin coatings utilized in conventional orthopedic casting systems include isocyanate-functional polyurethane prepolymers. Generally the resin coatings also include lubricants to facilitate unrolling, application, and molding without the resin interfering. Furthermore, they often include defoaming agents to maintain porosity while carbon dioxide is evolved during the curing process. When exposed to water, the isocyanate functional polyurethane prepolymers cure to form polyureas. In certain situations, it may be desirable to avoid or reduce the level of such reactive groups and their products.

Typical substrates upon which the above resin coatings are applied to produce an orthopedic casting tape are knit fabrics prepared from glass and/or synthetic fibers. Fiberglass or other high modulus fibers contribute significant strength to the cured resin/substrate composite as well as provide a reservoir for the resin during storage and end-use application of the casting tape. Nonglass low modulus substrates generally provide for a lower weight and more radiolucent cast. With most nonglass substrates the strength is limited by the amount of resin that can be held by the substrate. High resin loading with materials known to date must generally be avoided, however, to prevent excessive heat build-up in the cast while it is in its early stages of cure, i.e., during hardening, as a result of the exotherm produced in the above resins.

Typical orthopedic casting tapes are described in U.S. Pat. Nos. 4,667,661 and 4,774,937 (Scholz et al.), which are owned by Minnesota Mining and Manufacturing Company (3M Company) of St. Paul, Minn., the assignee of the present invention. Such tapes are also commercially available from 3M Company under the tradenames Scotchcast® Plus casting tape and Scotchcast® 3 casting tape. Construction materials of this type are also described in U.S. Pat. Nos. 4,411,262 and 4,570,622 (von Bonin et al.). These materials are one-component systems containing isocyanate or alkoxysilane groups selected from: (1) optionally substituted aminomethyl alkoxysilane, urea, or biuret derivatives; or (2) uretdione isocyanate functional alkoxysilanes.

A challenge with such conventional polyurethane prepolymer chemistry is to make a low viscosity resin with high strength and high lamination capabilities. That is, it can be difficult to overcome the rapid rise in viscosity with increasing functionality of either polyol or isocyanate, or with decreasing molecular weight of the polyol component. This rise in viscosity is likely due to the increase in hydrogen bonding from the increased concentration of urethane groups in combination with increased chain entanglements caused by increasing functionality.

A need exists for a water-curable resin composition that can be used in a wide variety of orthopedic support materials, whether used in combination with a fiberglass substrate or a nonglass low modulus substrate. That is, a need exists for a low viscosity resin composition that can be used in large amounts, i.e., at high resin loads, without excessive heat build-up, and/or perceived health hazards, as well as in smaller amounts.

SUMMARY OF THE INVENTION

The present invention provides a water-curable resin-coated sheet, preferably useable in a water-hardenable medical dressing capable of immobilizing and/or supporting a body part, i.e., as an orthopedic support material. This hardenable dressing can be used in tape, sheet, film, slab, or tubular form to prepare orthopedic casts, splints, braces, supports, protective shields, orthotics, and the like. Additionally, other constructions in prefabricated shapes can be used. As used herein the terms "orthopedic support material" or "orthopedic casting material" are used to encompass any of these forms of dressings, and "cast" or "support" are used to include any of these orthopedic support structures.

The water-hardenable orthopedic support material of the present invention is composed of a substrate coated or impregnated with a water-curable, low viscosity, resin composition. As used herein "water-curable" means that the resin composition is capable of hardening to a rigid, semi-rigid, or flexible structure on exposure to water such that the resin composition is no longer fluid, i.e., no longer flowable, at temperatures of use. Although water-cure can occur under a variety of conditions of temperature and pressure, it advantageously and preferably occurs at room temperature (about 20°–30° C.) and pressure (about 1 atmosphere pressure). Water can be provided by immersing in water, spraying, misting, or exposing the product to moist air, e.g., air with a relative humidity greater than about 10%.

Preferably, the water-curable, low viscosity, resin composition of the present invention has a viscosity of no greater than about 500 pascal-seconds (Pa-s), preferably no greater than about 200 Pa-s, more preferably no greater than about 125 Pa-s, and most preferably no greater than about 75 Pa-s, under ambient conditions, i.e., at a temperature of about 23° C. and atmospheric pressure (about 1 atm).

Preferably, the water-curable, low viscosity, resin composition contains less than about 1% solvent. As used herein "solvent" refers to low molecular weight (i.e., less than about 400 g/mole) volatile organic compounds (VOCs) and other liquids that function primarily to reduce resin viscosity, i.e., act as diluents and not as catalysts. That is, in preferred resin compositions there is less than about 1%, more preferably less than about 0.1%, most preferably less than about 0.01%, by weight of an organic solvent or other liquid viscosity-lowering compound present in the resin composition, based on the total weight of the resin composition. Optimally, the resin composition is substantially free of solvent.

The resin composition of the present invention is capable of curing to a thermoset state upon exposure to water to form a composite material at a temperature of about 10°–100° C., preferably about 20°–50° C. Furthermore, the resin composition is stable when stored at a temperature of less than about 40° C., i.e., it is storage stable. That is, it does not significantly increase in viscosity when stored at a temperature of less than about 40° C. If the resin viscosity increased during storage, the coated sheet material would be progressively more difficult to unwind, apply and mold to the patient.

The resin composition of the present invention consists primarily of a low viscosity, water-reactive resin, i.e., prepolymer or oligomer. The resin composition can also include an effective amount of a catalyst and other adjuvants such as lubricants, toughening agents, stabilizers, tackifiers, pigments, dyes, fillers, and fragrances. As used herein "an effective amount" of an adjuvant means an amount sufficient to provide one or more of the benefits of such an additive, as described herein.

The water-reactive resin is an alkoxysilane terminated resin, i.e., prepolymer or oligomer, having a number average molecular weight of about 400–10,000, preferably about 500–3,000. Each molecule of the prepolymer or oligomer contains at least one hydrolyzable terminal alkoxysilane group. Preferably, the alkoxysilane terminated resin is a urethane resin, i.e., a prepolymer containing —NH—C(O)—O—group(s), or a urea resin, i.e., a prepolymer containing —NH—C(O)—N—group(s), or a resin containing both urea and urethane groups. More preferably, the resin is urea/urethane-based.

The water-reactive alkoxysilane terminated prepolymer having at least one hydrolyzable terminal alkoxysilane group per molecule is preferably a compound of the formula (Formula I):

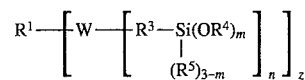

wherein:

Q is a polyol residue;

W is —NH—C(O)—X($R^2_{2-n-q}$)—or—X—C(O)—NH—;

X is —N—, —O—, or —S—;

Y is —N—, —O—, —S—, carbamylthio (—S—C(O)—NH—), carbamate (—O—C(O)—NH—), or substituted or N—substituted ureido (—N(C(O)—NH—)—);

$R^1$ is a substituted or unsubstituted divalent bridging $C_1$–$C_{200}$ hydrocarbon group, optionally interrupted in the backbone by 1–50 nonperoxide —O—, —C(O)—, —S—, —$SO_2$—, —$NR^6$—, amide (—C(O)—NH—), ureido (—NH—C(O)—NH—), carbamate (—O—C(O)—NH—), carbamylthio (—S—C(O)—NH—), unsubstituted or N—substituted allophonate (—NH—C(O)—N(C(O)—O—)—), unsubstituted or N—substituted biuret (—NH—C(O)—N(C(O)—N—)—), and N—substituted isocyanurate groups;

$R^2$ can be present or absent, and is selected from the group consisting of a H and a substituted or unsubstituted $C_1$–$C_{20}$ hydrocarbon group, optionally interrupted in the backbone by 1–10 nonperoxide —O—, —C(O)—, —S—, —$SO_2$—, or —$NR^6$—groups;

$R^3$ is a substituted or unsubstituted divalent bridging $C_1$–$C_{20}$ hydrocarbon group, optionally interrupted in the backbone by 1–5 nonperoxide —O—, —C(O)—, —S—, —$SO_2$—, or—$NR^6$—groups;

$R^4$ is a $C_1$–$C_6$ hydrocarbon group or —N=C($R^7$)$_2$;

each $R^5$ and $R^7$ is independently a $C_1$–$C_6$ hydrocarbon group;

$R^6$ is a H or a $C_1$–$C_6$ hydrocarbon group;

n=1–2 and q=0–1, with the proviso that when X is N, n+q=1, and when X is S or O, n+q=2;

u=the functionality of the polyol residue=0–6, with the proviso that when u=0, the compound of Formula I is

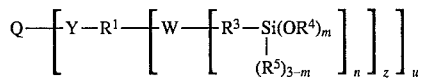

m=2–3; and z=1–3.

In the context of the present invention with respect to Formula I, the term "hydrocarbon" means an aromatic, heterocyclic, saturated or unsaturated linear, branched, or cyclic group. This term is used to encompass alkyl and vinyl groups, for example. Also included within the meaning of the term "hydrocarbon" as used herein are acyl groups, polyester groups, and poly(alkylene oxide) groups. The term "heterocyclic" means a mono- or polynuclear saturated or unsaturated cyclic radical containing carbons and one or more heteroatoms such as nitrogen, oxygen, phosphorus, silicon, or sulfur or a combination thereof in the ring or rings. The term "alkyl" means a monovalent residue remaining after removal of a hydrogen atom from a linear or branched chain saturated hydrocarbon. The term "cycloalkyl" means a monovalent residue remaining after removal of a hydrogen atom from a saturated cyclic hydrocarbon. The term "aromatic" or "aryl" means a monovalent residue remaining after removal of a hydrogen atom from an aromatic compound (single ring and multi- or fused-ring) including substituted aromatics such as lower alkaryl and aralkyl groups, lower alkoxy, N,N-di(lower alkyl)amino, nitro, cyano, halo, and lower alkyl carboxylic acid ester, wherein "lower" means a group having 1–4 carbon atoms. The term "acyl" means a monovalent organic residue remaining after removal of the OH from an aryl, alkyl, or cycloalkyl carboxylic acid. The term "alkenyl" means monovalent residue remaining after removal of a hydrogen atom from a linear or branched chain hydrocarbon containing at least one carbon-carbon double bond. The term "polyol residue" refers to the hydrocarbon group remaining after the active hydrogens of the polyol have reacted. The "functionality" of the polyol residue is the number of active hydrogen groups that reacted. As used herein, the term "polyol" includes compounds containing active hydrogens in accordance with the Zerevitinov test described in C. R. Noller, *Chemistry. Of Organic Compounds*, Ch. 6, pp. 121–122 (1957).

Suitable substrates onto which the resin composition is coated or impregnated include knit, woven, and nonwoven fabrics as well as foams and other porous materials. The fabric is generally formed in rolls of various widths, generally about 1–8 inches (2.5–20.3 cm) in width. The fabric is coated or impregnated with the water-curable solventless resin composition in an amount of generally about 0.6–5 times the weight of the material forming the fabric. Preferably, this is in an amount of about 40–300 g/m$^2$, and more preferably about 100–200 g/m$^2$. As used herein "impregnate" refers to a condition in which the resin composition is thoroughly intermingled with, and in surrounding relation to, the fibers or filaments of the fabric. Generally, the resin composition flows into some of the spaces in the fabric between the fibers or filaments. Upon curing, the resin composition generally becomes bonded, physically or chemically, to the fabric, forming a composite material although leaving sufficient permeability to air to render the cured fabric breathable.

DETAILED DESCRIPTION OF THE INVENTION

Figure 1:
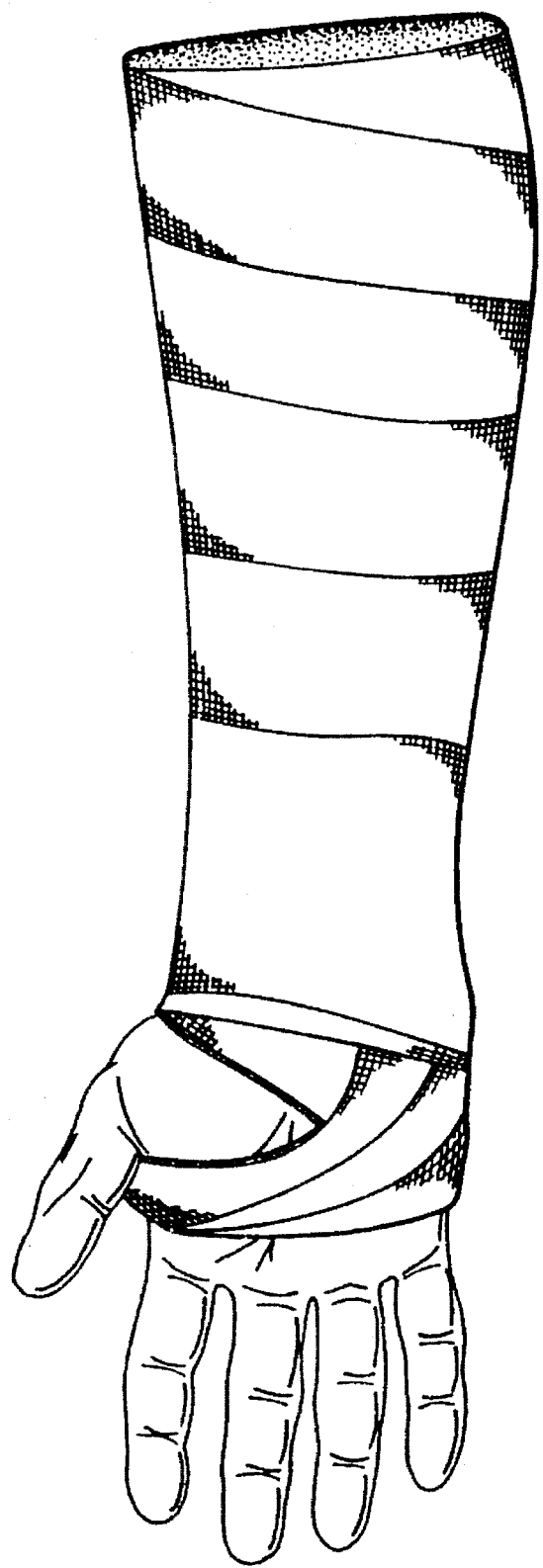
FIG. 1 is a schematic representation of the casting material of the present invention shown wrapped in position for cure.

As indicated above, conventional orthopedic casting materials generally comprise a substrate having isocyanate functional polyurethane prepolymer resins distributed therein. Upon exposure to water, the resin will cure with the evolution of heat forming a hard tough polyurea urethane. Such compositions are described for example in U.S. Pat. No. 4,502,479 (Garwood et al.), U.S. Pat. No. 4,619,578 (Reed), U.S. Pat. No. 4,667,661 (Scholz et al.), and U.S. Pat. No. 4,774,937 (Scholz et al.), each of these references being incorporated herein by reference. The present invention provides generally fast-curing coated substrates, particularly at room temperature, that remain relatively cool during cure, i.e., having low exothermic reaction temperatures.

Suitable resin compositions for use in the orthopedic casting materials, e.g., tapes, of the present invention preferably have the following properties: (1) substantial storage life; (2) low toxicity; (3) appropriate viscosity and flow characteristics that allow it to coat the substrate and remain in place, on and within the substrate, while in storage and during cure but not so high that the tape is unduly hard to unroll and apply; (4) water-curable, i.e., curable upon exposure to moisture in the air, upon soaking or spraying with water, or through some similar action; (5) fast cure rate, i.e., set-up preferably within 3–5 minutes and at least within 2 to 15 minutes to the shape of the body part, and cure to form a weight-bearing cast within a period of about 30 minutes to several hours; (6) cure to a relatively strong, tough, and long lasting cast such that the cast is sufficiently strong (whether flexible, semi-rigid, or rigid) to support a fractured limb; (7) cure without the generation of substantial heat that can harm the patient; (8) cure to a substantially waterproof cast, i.e., a cast that will not soften to the extent that the cast breaks down during normal use or delaminate upon contact with water after cure; (9) cure to form a cast that can be readily removed without discomfort to the patient; (10) cure with little shrinkage of the cast; (11) nontacky upon contact with water; (12) minimal or nonoffensive smell; (13) free of offensive or noxious organic solvents; (14) reasonable work life such that there is a reasonable period of time in which to mold the material to the limb; (15) reasonable flexibility in the uncured state such that the material readily assumes the shape of the limb during application; and (16) does not cause skin irritation as a result of chemical irritation. The present invention concerns the development and identification of such a resin composition.

Curable resin compositions for use in orthopedic casting tapes according to the present invention generally include compositions composed of a water-reactive resin, i.e., polymer or oligomer, having at least one terminal hydrolyzable alkoxysilane group. The resin composition is flowable such that it coats a substrate and remains in place, on and within the substrate, while in storage and during cure. Generally, the resin composition has a viscosity of no greater than about 500 Pa-s and at least about 5 Pa-s, i.e., a viscosity of about 5–500 Pa-s. Preferably for use as an impregnant for typical fabrics employed as orthopedic casting tapes, the resin composition of the present invention has a viscosity of no greater than about 200 Pa-s, more preferably no greater than about 125 Pa-s, and most preferably no greater than about 75 Pa-s. Although generally, the resin composition of the present invention has a viscosity of at least about 5 Pa-s, preferably the viscosity is at least about 10 Pa-s, under ambient conditions, i.e., at about 23° C. and 1 atmosphere pressure. The viscosity measurements made herein are measured using a Brookfield RVT Rotovisco viscometer and spindles 5, 6, or 7 at low speed (less than 20 rpm). For resin compositions under 100 Pa-s, a Brookfield RVT Rotovisco viscometer with spindle #6 at 10 rpm is used. For resins over 100 Pa-s, spindle #7 is used.

Upon hardening, the resin compositions of the present invention generate little or no patient-detectable heat, thereby lessening the possibility of harm to the patient upon curing of the resin. That is, the resin compositions exotherm at a temperature less than about 50° C., preferably less than about 45° C., more preferably less about 40° C., and most preferably less than about 30° C. They also cure without extensive foaming and evolution of $CO_2$. The practical result of the generation of little heat and $CO_2$ upon curing is that the casting material can include a larger amount of resin, i.e., there can be a higher coating weight on the substrate if desired. The larger amount of resin provides additional strength to the resultant orthopedic support. This is of particular utility when a low modulus organic substrate is used, such as a polyester fabric, which provides lighter weight casts and increased radiolucency. Also, the cured compositions retain most of their strength in the presence of water and heat.

Preferably, the water-curable, low viscosity, resin composition contains less than about 1% solvent. As used herein "solvent" refers to low molecular weight (i.e., less than about 400 g/mole) volatile organic compounds (VOCs) and other liquids that function primarily to reduce resin viscosity, i.e., as diluents and not as catalysts. That is, in preferred resin compositions there is less than about 1%, more preferably less than about 0.1%, and most preferably less than about 0.01%, by weight of an organic solvent or other liquid viscosity-lowering compound present in the resin composition, based on the total weight of the resin composition. Optimally, the resin composition is substantially free of solvent.

In this way, the resin compositions of the present invention incorporate little (preferably less than about 1%, more preferably less than about 0.1%, most preferably less than about 0.01%), if any, organic solvents, diluents, or dispersants, such as, for example, methanol, dioxane, tetrahydrofuran, 2-ethoxyethanol, 2-methoxyethanol. Furthermore, they incorporate little (preferably less than about 1%, more preferably less than about 0.1%, most preferably less than about 0.01%), if any, liquid organometallic solvents, diluents, or dispersants, such as, for example, trimethyl borate, tetramethoxysilane, and tetraethoxysilane. It is to be understood that the resin composition contains little (preferably less than about 1%, more preferably less than about 0.1%, most preferably less than about 0.01%), if any, solvent prior to cure of the prepolymer. That is, there is little (preferably less than about 1%, more preferably less than about 0.1%, most preferably less than about 0.01%), if any, solvent in the resin composition as it exists prior to exposure to water. During cure of the prepolymer, however, the resin composition can contain a solvent because volatile organic compounds such as methanol and ethanol can be produced as condensation reaction products.

The resin composition of the present invention consists primarily of a low viscosity, water-reactive resin, i.e., prepolymer or oligomer. That is, the resin composition of the present invention includes about 70–100 wt-% prepolymer or oligomer, based on the total weight of the resin composition. The resin composition can also include an effective amount of a catalyst and other adjuvants such as slip agents, toughening agents, stabilizers, tackifiers, pigments, dyes, and fragrances. Furthermore, the resin composition can include an effective amount of one or more fillers or other insoluble adjuvants, i.e., materials not soluble or miscible with the resin.

The water-reactive resin is an alkoxysilane terminated resin, i.e., prepolymer or oligomer, having a number average molecular weight of about 400–10,000, preferably about 500–3,000. A polymer forms upon contacting the alkoxysilane terminated prepolymer with water as a result of condensation of molecules of this prepolymer with other molecules of the same prepolymer. Each molecule of the prepolymer or oligomer contains at least one hydrolyzable terminal alkoxysilane group. Compounds of Formula I useful in the resin compositions of the present invention may contain one to six terminal alkoxysilane groups per molecule. Preferably, the alkoxysilane terminated resin is a urethane-based resin, i.e., a prepolymer containing —NH—C(O)—O— group(s), or a urea resin, i.e., a prepolymer containing —NH—C(O)—N— group(s), or a resin containing both urea and urethane groups. More preferably, the resin is urea/urethane-based.

The water-reactive alkoxysilane terminated resin having at least one hydrolyzable terminal alkoxysilane group per molecule is preferably a compound of the formula (Formula I):

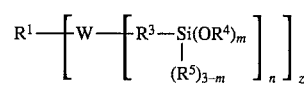

wherein:

Q is a polyol residue;

W is —NH—C(O)—X($R^2_{2-n-q}$)— or —X—C(O)—NH—;

X is —N—, —O—, or —S—;

Y is —N—, —O—, —S—, carbamylthio (—S—C(O)—NH—), carbamate (—O—C(O)—NH—), or substituted or N-substituted ureido (—N(C(O)—NH—)—);

$R^1$ is a substituted or unsubstituted divalent bridging $C_1$–$C_{200}$ hydrocarbon group, optionally interrupted in the backbone by 1–50 nonperoxide —O—, —C(O)—, —S—, —SO$_2$—, —NR$^6$—, amide (—C(O)—NH—), ureido (—NH—C(O)—NH—), carbamate (—O—C(O)—NH—), carbamylthio (—S—C(O)—NH—), unsubstituted or N—substituted allophonate (—NH—C(O)—N(C(O)—O—)—), unsubstituted or N—substituted biuret (—NH—C(O)—N(C(O)—N—)—), and N—substituted isocyanurate groups;

$R^2$ can be present or absent, and is selected from the group consisting of H and a substituted or unsubstituted $C_1$–$C_{20}$ hydrocarbon group, optionally interrupted in the backbone by 1–10 nonperoxide —O—, —C(O)—, —S—, —SO$_2$—, or —NR$^6$—groups;

$R^3$ is a substituted or unsubstituted divalent bridging $C_1$–$C_{20}$ hydrocarbon group, optionally interrupted in the backbone by 1–5 nonperoxide —O—, —C(O)—, —S—, —SO$_2$—, or —NR$^6$—groups;

$R^4$ is a $C_1$–$C_6$ hydrocarbon group or —N=C($R^7$)$_2$;

each $R^5$ and $R^7$ is independently a $C_1$–$C_6$ hydrocarbon group;

$R^6$ is a H or a $C_1$–$C_6$ hydrocarbon group;

n=1–2 and q=0–1, with the proviso that when X is N, n+q=1, and when X is S or O, n+q=2;

u=the functionality of the polyol residue=0–6, with the proviso that when u=0, the compound of Formula I is

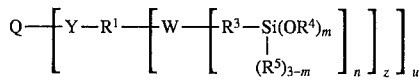

m=2–3; and z=1–3.

It is to be understood that each "$R^3$—Si($R^5$)$_{3-m}$(OR$^4$)$_m$" moiety can be the same or different. When used in Formula I, the Y and $R^1$ groups that are not symmetric, e.g., amide (—C(O)—NH—) and carbamylthio (—S—C(O)—NH—) groups, are not limited to being bound to adjacent groups in the manner in which these groups are represented herein. That is, for example, if $R^1$ is carbamate (represented as —O—C(O)—NH—), it can be bound to Y and W in either of two manners: —Y—O—C(O)—NH—W— and —W—O—C(O)—NH—Y—.

Herein, when it is said that "each" $R^5$ and $R^7$ is "independently" some substituent group, it is meant that generally there is no requirement that all $R^5$ groups be the same, nor is there a requirement that all $R^7$ groups be the same. As used herein, "substituted" means that one or more hydrogen atoms are replaced by a functional group that is nonreactive, e.g., to hydrolysis and/or condensation and noninterfering with the formation of the cured polymer.

In preferred materials $R^1$ is selected from the group consisting of a substituted or unsubstituted $C_1$–$C_{200}$ alkyl, a substituted or unsubstituted $C_1$–$C_{200}$ acyl, and groups of up to 50 multiples of a $C_3$–$C_{20}$ cycloalkyl, a $C_7$–$C_{20}$ aralkyl, and a $C_6$–$C_{18}$ aryl. By this, it is meant that $R^1$ can be a long chain containing, for example, up to 50 repeating $C_6$–$C_{18}$ aryl groups. More preferably, $R^1$ is selected from the group consisting of a substituted or unsubstituted $C_1$–$C_{100}$ alkyl, a substituted or unsubstituted $C_1$–$C_{100}$ acyl, and groups of up to 30 multiples of a $C_5$–$C_8$ cycloalkyl, and a $C_6$–$C_{10}$ aryl. Most preferably, $R^1$ is selected from the group consisting of a $C_1$–$C_{20}$ alkyl, a $C_1$–$C_8$ acyl, and groups of up to 5 multiples of a $C_5$–$C_8$ cycloalkyl, and a $C_6$–$C_{10}$ aryl. In each of the preferred $R^1$ groups, the backbone is optionally interrupted by 1–20 nonperoxide —O—, —C(O)—, —S—, —SO$_2$—, —NR$^6$—, amide, ureido, carbamate, carbamylthio, allophonate, biuret, and isocyanurate groups.

In each of the more preferred $R^1$ groups, the backbone is optionally interrupted by 1–10 nonperoxide —O—, —C(O)—, —S—, —SO$_2$—, —NR$^6$—, amide, ureido, carbamate, carbamylthio, allophonate, biuret, and isocyanurate groups. In each of the most preferred $R^1$ groups, the backbone of each of the $R^1$ groups is not interrupted by any of these groups.

In preferred materials, each of $R^2$ and $R^3$ is independently selected from the group consisting of a substituted or unsubstituted $C_1$–$C_{20}$ alkyl, a substituted or unsubstituted $C_2$–$C_{18}$ alkenyl, and groups of up to 10 multiples of a $C_3$–$C_{18}$ cycloalkyl and a $C_6$–$C_{18}$ aryl. More preferably, each $R^3$ and $R^2$ is independently selected from the group consisting of a substituted or unsubstituted $C_1$–$C_{10}$ alkyl, a substituted or unsubstituted $C_2$–$C_{10}$ alkenyl, a $C_5$–$C_8$ cycloalkyl, and a $C_6$–$C_{10}$ aryl. Most preferably, each $R^2$ and $R^3$ is independently selected from the group consisting of a $C_1$–$C_6$ alkyl, a $C_2$ alkenyl, a $C_5$–$C_8$ cycloalkyl, and a $C_6$ aryl. In each of the preferred $R^2$ and $R^3$ groups, the backbone is optionally interrupted by 1–5 nonperoxide —O—, —C(O)—, —S—, —SO$_2$—, and —NR$^6$—groups. In optimal resins, the backbone of each of the $R^2$ and $R^3$ groups is not interrupted by any of these groups.

In preferred materials, each of $R^4$, $R^5$, $R^6$, and $R^7$ is independently a $C_1$–$C_6$ alkyl group. More preferably, each is a $C_1$–$C_3$ alkyl group. A single prepolymer according to Formula I can be used in the resin composition of the present invention. Alternatively, a mixture of several different prepolymers according to Formula I can be used in the resin composition.

One preferred embodiment of the present invention consists of a urethane-based resin containing highly functionalized silane groups and a catalyst. This resin can be prepared, for example, from the reaction of an isocyanate-containing compound and an alkoxysilane or from an isocyanatoalkylalkoxy silane and an alcohol-functional polyol. Preferably, preferred resins of the present invention are prepared from isocyanate end capped polyols and alkoxyaminosilanes. For example, the resin can be prepared from a reaction in which the isocyanate groups of toluene diisocyanate (TDI) based prepolymers are end-capped with the difunctional aminosilane bis(trimethoxysilylpropyl)amine (Scheme 1). Alternative resin formulations can be based on amine-functional polyols, such as Jeffamine (available from Texaco) and mercaptofunctional polyols.

Scheme 1

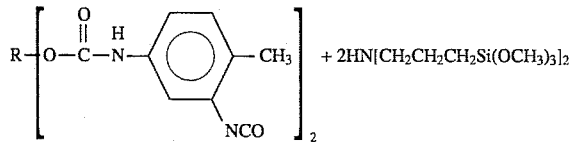

R = Polyol

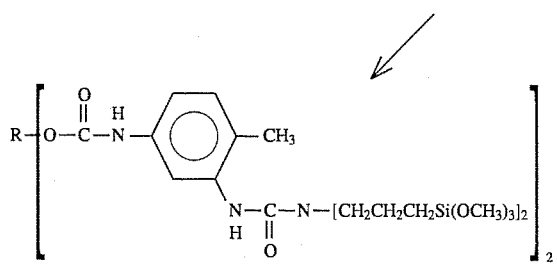

Preferred isocyanates upon which the isocyanate-containing compounds are based are asymmetrical in the sense that there is a significant differential reactivity between the isocyanate groups. That is, the isocyanates contain at least one isocyanate group which is significantly more reactive than one or more on the same molecule by a factor of 2 or more. The preferred isocyanates, on which the isocyanate-containing compounds are based, have a functionality of 2–3, while particularly preferred materials have functionalities of 2–2.3. The presently preferred isocyanate is TDI. Other aromatic isocyanates such as MDI and polyisocyanates based on condensation products of formaldehyde and aniline are potentially useful. Aliphatic isocyanates are useful and may be particularly preferred for applications where stability to UV light is of particular concern.

Materials such as the trimer and biuret adducts of HMDI, methylene-bis-(4-cyclohexylisocyanate), 4,4',4–triphenylmethane triisocyanate, tetramethylxylene diisocyanate (TMXDI), xylene diisocyanate could be used in the preparation of the isocyanate-containing compounds used in the preparation of the resin of the present invention. Materials such as isophorone diisocyanate, 3-methyl 4,4'-methylene diisocyanate, and the like are perhaps particularly useful due to the differential reactivity of the isocyanate groups. Other isocyanates that can be used are disclosed in J. H. Saunders et at., *Polyurethanes Chemistry and Technology*, Robert E. Krieger Publishing Co., Malabar, Fla. (1987).

Note that the reaction could be carried out with any one particular polyol at higher NCO/OH ratios, however, since substantially all of the isocyanate is end capped in the subsequent reaction shown in Scheme 1. The concentration of hydrogen bonding urea (or thiourethane) groups would increase significantly, further increasing the resin viscosity as a result of higher NCO/OH ratios.

The differential reactivity of the isocyanates in toluene diisocyanate, for example, allows for the preparation of 2:1 adducts of diisocyanate and polyol in these TDI-based prepolymers with low levels of chain extension. This has the effect of giving low molecular weight (MW) prepolymers as opposed to higher MW oligomers that are attained with symmetrical isocyanates, such as 4,4'-diphenylmethane diisocyanate (MDI) and 1,6-hexamethylene diisocyanate, which have isocyanate functional groups of approximately the same relative reactivity. The result of using assymetric isocyanates is lower viscosity.

In order to further reduce resin viscosity the alkoxyamino silanes preferably contain secondary amines. A secondary amine containing alkoxysilane functionality is exemplified in Scheme 1. Secondary amines are preferred to give an adduct that contains fewer N—H bonds. The smaller number of these bonds precludes significant hydrogen bonding among the polymer chains and hence lowers the viscosity of these systems considerably compared to using a primary aminosilane.

The preferred TDI-based isocyanate containing compounds have very little free TDI monomer, typically less than about 0.1%. When reacted with an alkoxyaminosilane, the resulting resin has extremely low, and typically no, detectable residual TDI. Although excess alkoxysilane can be employed in the preparation of the preferred resins of the present invention, the amount of alkoxysilane used is preferably kept low. This is particularly advantageous if the silane is volatile because of improved resin odor and safety. In addition, alkoxysilane functional monomers in significant excess can reduce the strength of the resultant resin.

Isocyanate-containing compounds are available from Air Products and Uniroyal with free NCO functionality ranging from 1.9–9.0%. As stated above, preferred isocyanate-containing compounds are polyols. Such compounds are available containing polypropylene glycol, polytetramethylene glycol, and polyester ether polyols. Particularly preferred isocyanate-containing compounds are diiosocyanate compounds containing polytetramethylene glycol. The resin of the present invention should not be limited to this particular polyol, but include polyether polyols such as polyethylene glycol, polypropylene glycol, polybutylene glycol, and random or block copolymers of these and polymer polyols such as those disclosed in U.S. patent application Ser. No. 07/376, 421, filed on Jul. 7, 1989.

Polyolefin polyols, such as polybutadiene polyols and polyisoprene polyols, can be used in the preparation of the isocyanate-containing polyols. Furthermore, aromatic and aliphatic amine-terminated "polyols" such as Jeffamine and Polamine materials can be used. Low molecular weight polyalcohols, polyamines, and polythiols can also be used as chain extenders. Mixtures and blends of these polyols may be useful. The preferred average polyol functionality is 1.8–3, more preferably 2–2.5. It is understood, however, that polyols with functionalities as high as 4 or more may be useful.

Typical silanes include, but are not limited to, N-(dimethoxymethylsilylisobutyl)ethylenediamine, gamma-aminopropylmethyldimethoxysilane, 3-aminopropyltriethoxysilane, N-methylaminopropyltrimethoxysilane, N-phenylaminopropyltrimethoxysilane, delta-aminobutylmethyldiethoxysilane, 3-mercaptopropylmethyldimethoxysilane, 1-trimethoxysilyl-2-(3,4-aminoethyl)phenylethane, aminophenyltrimethoxysilane, omega-aminoundecyltrimethoxysilane, and 3-(4-aminophenoxy)propyltrimethoxysilane. One preferred reactive silane of the present invention is bis(trimethoxysilylpropyl)amine, but other reactive silanes could be employed such as aminopropyltrimethoxysilane, N-beta-(aminoethyl)-gamma-aminopropyltrimethoxysilane, gamma-mercaptopropyltrimethoxysilane, etc. Preferred silanes are trimethoxy- and triethoxy silanes but other trialkoxy, alkyldialkoxy, aryldialkoxy, and oximino silanes could be useful in the preparation of the resin of the present invention. These could also be reacted in various combinations and proportions with the TDI-based compounds to produce a wide range of average silane functionality (2–4 or more).

Catalysts

The resin compositions of the present invention include an effective amount of a catalyst or mixture of catalysts. The catalysts can be acid catalysts, base catalysts, or metal-containing catalysts. Generally, the catalyst, or mixture of catalysts, is present in the resin composition of the present invention in an amount to catalyze the polymerization of the alkoxysilane terminated resin upon contact with water. Preferably, the catalyst, or mixture of catalysts, is present in an amount of about 0.1–10 wt-%, and more preferably in an amount of about 1–5 wt-%, and most preferably 2–3 wt-%, based on the total weight of the resin composition.

Preferred catalysts are basic inorganic or organic compounds. Preferably, the basic catalysts are strong organic bases, i.e., having a pKa greater than about 9. More preferably, the strong organic basic catalysts have a pKa greater than about 10, and most preferably greater than about 11. In optimal systems, the strong organic basic catalyst has a pKa greater than about 12.

Substituted guanidines are preferred basic catalysts for the preferred resins and tetrasubstituted guanidines are more preferred. It has been found that N,N,N',N'-tetramethylguanidine (TMG) is a particularly preferred catalyst for these silane cure systems ensuring a sufficiently rapid hydrolysis of the alkoxysilane groups and subsequent condensation of the resulting silanols to form siloxane adducts. However, other basic catalysts could be used in this resin composition such as: inorganic bases, e.g., calcium hydroxide, magnesium hydroxide, and the like; quaternary ammonium bases, such as tetrabutylammonium hydroxide; tertiary amine catalysts, such as N,N-dimethylcyclohexylamine, triethylenediamine, and triethylamine; bisaminoethers, such as bis(dimethylaminoethyl) ethers; amidine bases, such as 1,5-diazabicyclo[4,3,0]non-5]ene (DBN) and 1,8diazobicyclo[5,4,0]undecan-7-one (DBU); and other N-containing heterocycles, such as piperazines, imidazoles, piperidines, etc.

Acid catalysts can also be used. Preferably the acid catalysts are strong acids, i.e., having a pKa of no greater than about 5. More preferably, the acid catalysts have a pKa of no greater than about 3, and most preferably, no greater than about 1. This includes, for example; sulfonic acids (including alkyl and perfluoroalkyl); carboxylic acids (including alkyl and perfluoroalkyl); phosphoric acids; boric acids; and the like.

Moreover, various metal catalysts such as ligands of tin, cobalt, bismuth, lead, zinc or titanium which are known to the art of alkoxysilane cure could be used alone or in combination with the afore-mentioned catalysts in this resin system. Some examples include dibutyltin dilaurate, dibutyltin diacetate, dibutyltin dimethoxide, tin octoate, dibutyltin di-2-ethylhexoate, dioctyltin dilaurate, zinc 2-ethylhexoate, zinc stearate, zinc laurate, zinc naphthanate, titanium naphthanate, 1,3,propenedioxytitanium, bis(acetylacetanate), tetrabutyl titanate, titanate esters shown in U.S. Pat. No. 4,889,903, zirconium octoate, cobalt 2-ethylhexoate, bismuth octoate, bismuth stearate, bismuth neodecanoate, and 1,3-propanidioxytitanium bis(ethylacetoacetate).

While to date the preferred method is to use the amine catalyst as an additive, it could also be reacted into the polymer and act as a polymer-bound catalyst. Either the acid or base catalysts, or the metal catalyst, can be bound into the polymer backbone, as long as the pKa of the catalyst is not altered significantly upon incorporation into the polymer. In one example the TMG is added to the isocyanate functional prepolymer prior to or along with the alkoxysilane to allow the isocyanate to react with the free amine on TMG. The substituents about the guanidine could also be varied to improve the properties of the catalyst as well as to generate a polymer-bound catalyst. Furthermore, the TMG could be reacted with a silane such as glycidoxypropyltrialkoxy silane as discussed in U.S. Pat. No. 4,954,598 or chloropropyl trialkoxysilane as discussed in U.S. Pat. No. 4,180,642 to allow it to bind into the polymer backbone after the material has been activated with water.

Adjuvants

Preferred compositions according to the present invention can include a variety of adjuvants therein. It is foreseen that adjuvants such as surfactants, lubricants or tack reducing agents, toughening agents, fillers, pigments (or dyes), and/or fragrances will most typically be used. Certain adjuvants, e.g., surfactants, lubricants, dyes, etc., may be soluble, insoluble, or covalently bound to the polymer backbone. Fillers may be surface treated using silanes, zirconates, titanates, etc.

Tack Reducing Agents

The useful curable resin compositions of the present invention may also include a lubricant as a tack reducing agent. Such agents are disclosed in U.S. Pat. Nos. 4,774,937 and 4,667,661, which are incorporated herein by reference. As used herein, the term "lubricant" refers to a material which when added to the formulation provides a resin coated sheet material having reduced tack, i.e., a material which when immersed in water quickly becomes slippery and unwinds from a roll easily. Lubricants may be hydrophilic groups which are covalently bound to the resin, or an additive which is incompatible with the curable resin such as a surfactant (as described in U.S. Pat. No. 4,667,661, which is incorporated herein by reference), a polymer comprised of hydrophilic groups, a polysiloxane, or a combination of these materials. Preferred agents include, but are not limited to, poly(ethylene oxide), butylene oxide-ethylene oxide block copolymers, polymers including hydrophilic groups, propylene oxide-ethylene oxide block and random copolymers, and polydialkylsiloxanes. More preferred are polyoxyalkylene alkyl ethers known as Brij® compounds sold by Aldrich under an ICI trademark, and most preferred are Brij® 35 (polyoxyethylene(23) lauryl ether) and Brij® 58 (polyoxyethylene(20) cetyl ether). Generally, if a lubricant is used at all, what is required is that an amount of the agent(s) be used to achieve the desired effect of reduced tack prior to and/or during cure, such that the resin does not stick to the hands of the medical practitioner. To achieve this result, the amount of lubricant(s) used is typically about 1–10 wt-%, preferably about 2–6 wt-% based on the total weight of the resin composition.

Toughening Agents

Toughening agents may also be included in the curable resin compositions of the present invention to increase the strength of the cured material. As used herein, the term "toughening agent" refers to a material which when added to the resin increases the total energy input per unit volume of material required to cause failure. Such agents can include carboxy, amine, methacrylate, and vinyl terminated butadiene-acrylonitrile polymers known as Hycar® reactive liquid polymers available from B. F. Goodrich (Cleveland, Ohio). Thermoplastics such as styrene-butadiene copolymers available from Shell Chemical Co. (Houston, Tex.), polyurethanes, and polytetrafluoroethylene can also be useful as toughening agents. In addition, core/shell polymers such as those having an internal rubbery phase and surrounded by a thermoplastic phase. For example, graft polymers having a rubbery core, such as a styrene-butadiene block copolymer, and a poly(meth)acrylate shell, available for example as BTA IIIF from Rohm & Haas (Philadelphia, Pa.), may be useful as toughening agents in the curable resins of the present invention. Furthermore, plasticizers such as dioctyl phthalate and butyl benzyl phthalate may be used to soften, reduce brittleness and thereby toughen the cured material. Generally, if a toughening agent is used at all, what is required is that an amount of the agent be used to achieve the desired effect. Typically, up to about 50 wt-%, preferably up to about 10 wt-%, is used in the resin compositions of the present invention.

Fillers

Fillers may also be used in the curable resin compositions to increase strength of the cast obtained, reduce cost, and alter viscosity, thixotropy or overall fluid flow properties of the curable resin. Fillers can also be used to modify appearance and handling characteristics of the coated sheet material. Useful fillers include, but are not limited to, particulate, spherical, fibrous, micro fibrous, flake, or platelet forms including aluminum oxides, calcium metasilicate, titanium dioxide, fumed silica, zeolites, amorphous silica, ground glass, glass fibers, glass bubbles, glass microspheres or mixtures of these materials. Additional fillers include particles of polypropylene, polyethylene, or polytetrafluoroethylene. In general, if a filler is used at all, what is required is that enough filler be used to achieve the desired effect. Typically, up to about 25 wt-%, preferably about 5–20 wt-%, and more preferably about 5–15 wt-%, is used in the resin compositions of the present invention. Calcium metasilicate fillers are particularly preferred in the case of rigid orthopedic casting tape materials and are discussed in commonly assigned, copending U.S. application Ser. No. 08/8755, filed on Jan. 25, 1993, incorporated herein by reference.

Colorants

The color of the curable resin composition of the present invention may be effected by colorants, such as inorganic pigments, organic pigments, fluorescent and luminescent pigments, and dyes. Suitable colorants include those disclosed in U.S. Pats. 5,005,566 and 5,052,380. Hydroxyfunctional colorants may be chemically bound into the curable resin composition by condensation with —SiOH groups on the polymer, exchange with an —SiOR group or reaction with a suitable reactive silane such as an epoxy or isocyanatosilane (amino-thiol functional colorants could be bound in a similar fashion). In general, if pigments or dyes are used at all, what is required is a sufficient amount of the pigments or dyes to achieve the desired effect. Typically, up to about 10 wt-% colorant can be used in the resin compositions of the present invention.

Fragrance

It may be desirable to include a fragrance in the resin to make the experience of having a cast put on more pleasant for the patient and to mask unpleasant odors that may arise after prolonged wear from body odor and microorganisms. Examples of fragrances which may be included are lemon, peach, strawberry, apricot, fruit punch, cinnamon, juniperberry, baby powder, sandalwood, and frankincense. Such fragrance additives are available from Stanley S. Schoenmann, Inc. (Clark, N.J.), Berje (Bloomfield, N.J.) and Atlanta Fragrance, Inc. (Marietta, Ga.). In general, if a fragrance is desired at all, what is required is sufficient amount of fragrance to achieve the desired effect. Typically, up to about 1.0 wt-%, preferably up to about 0.5 wt-%, of fragrance is used in the resin compositions of the present invention.

Preparation of the Resin Compositions

The isocyanate-containing compounds, such as the isocyanate-containing polyols available as Airthanes from Air Products or Adiprenes from Uniroyal, are mixed with the alkoxysilane along with any other additive (i.e., filler, lubricant, etc.) at approximately room temperature. The mixture is then well agitated until homogeneous, typically about 1–5 minutes. The reaction typically exotherms, so the exotherm is kept in the 120°–170° F. (49–77° C.) temperature range. This is typically accomplished by occasional placement in a cold water bath. After allowing the components to mix until fully reacted, e.g., for about 16–24 hours (preferably on a roller machine at 16 rpm), a catalyst is mixed into the resin until homogeneous. Typically this can be accomplished at room temperature via a high shear mixer or at 175°–195° F. (79°–91° C.) via an overhead stirrer. The resin composition is then ready for coating on a suitable scrim.

Preparation of the Uncured Casting Material

The uncured casting material generally comprises a substrate or scrim impregnated with the uncured resin composition. In general, it is desired that the casting tape be constructed from a fabric or substrate which is relatively stretchable and flexible; i.e., which has a lengthwise extensibility of at least about 20%, preferably about 40–60%, once coated with the uncured resin. This will facilitate fitting the casting tape around contoured portions of the body, such as the heel, knee or elbow. Furthermore, it is desired that the casting tape be constructed from a porous or mesh fabric, i.e., a fabric having apertures of sufficient size to enable water to permeate the roll of casting tape during water activation and cause the resin to set after application to a body part or other structure. In addition, a porous fabric is desired to allow air and moisture vapor to move through the material after cure, thereby promoting patient comfort and avoiding skin breakdown caused by excessive moisture build-up under the cured material. Suitable aperture sizes are about 0.3–16 mm$^2$, preferably about 1.2–9 mm$^2$. The fabric has 7.75–77.5 apertures/cm$^2$, more preferably about 15.5–62 apertures/cm$^2$, and most preferably about 23–39 apertures/cm$^2$. Where an impermeable occlusive wrap is desired, a nonapertured fabric may be used. In this case, water may be added to the coated material as it is applied for optimum cure speed.

Suitable substrates include knit, woven, and nonwoven fabrics as well as foams and other porous materials made of natural or synthetic fibers. Examples of preferred fiber materials from which flexible casting tapes can be formed include, but are not limited to, fiberglass, silane-treated fiberglass, nylon, polyolefins, polyamides, polyesters, cotton, rayon, and mixtures thereof. Other usable materials include knits, wovens, and nonwovens any of which may contain elastic yarns or fibers of natural rubber, synthetic rubber, or polyurethane. Preferred fabrics obtain extensibility through mechanical compaction such as microcreping or through the use of heat shrinkable highly twisted texturized yarns. Fabrics such as these are disclosed in commonly assigned, copending U.S. application Ser. No. 08/9923 filed Jan. 25, 1993, incorporated herein by reference. The backings may be dyed or pigmented in a solid or patterned manner, as discussed in commonly assigned, copending U.S. application Ser. No. 751,725, filed Aug. 29, 1991, now U.S. Pat. No. 5,342.291, incorporated herein by reference.

A more preferred fiber material from which stretchable casting tapes can be formed is fiberglass. Fiberglass is relatively strong and inexpensive. When used with the water-curable resin of the present invention, the combination cures to a very hard, lightweight, strong, weight-beating cast. While fiberglass yarns themselves are relatively inelastic, they can be knitted into a highly extensible knit fabric or substrate. Fiberglass woven or knitted substrates suitable for use in casting tapes according to the present invention include those used in the knitted substrate of Scotchcast® Plus casting tape, which tape is available from 3M Company (St. Paul, Minn.). Other preferred fiberglass fabrics are those discussed in U.S. Pat. No. 4,668,563. Another preferred fabric is nonfiberglass and is disclosed in Ersfeld et al., U.S. Pat. No. 4,841,958, wherein an apermred nonwoven fabric is described. Yet another preferred fabric is a non fiberglass knitted material described in U.S. Pat. No. 4,940,047 (Richter et al.).

The substrate can be coated or impregnated with the resin composition by any of a variety of means well known in the art, depending on the viscosity of the resin composition. It is understood that the fabric must be dry (i.e., free of moisture) and must be coated in an inert atmosphere or under dry conditions, e.g., relative humidity less than 4–6%. For example, low viscosity compositions can be sprayed onto a substrate. A resin composition of high viscosity can be applied to a substrate as a putty. A resin composition of moderate viscosity can be applied to a substrate by brush, knife coating, curtain coating or with a roll coater. Resins may be applied at room temperature or at elevated temperature (generally less than about 100° C.). Coating must typically be done in such a manner that excessive exposure to moisture is avoided to prevent curing of the resin.

As a typical example, the resin composition is applied to a substrate by spreading the resin onto the surface of the substrate by knife coating or other similar method and allowing the resin to wick and soak into the substrate. Some manipulation such as pressuring or kneading of the resin into the substrate may sometimes be desirable.

The amount of the resin composition applied to the substrate can vary considerably depending on the actual viscosity of the composition and the end use of the material. Typically, the fabric is impregnated with the water-curable resin composition in an amount of about 40–300 g/m$^2$, preferably about 100–200 g/m$^2$, of the material forming the fabric. More preferably, fiberglass fabric is used and impregnated with the resin composition in an amount of about 31–55% by weight of the impregnated casting material.

A variety of conventional techniques can be utilized to store the uncured resin-coated substrate, prior to use to form a cast. Typically a roll of the coated substrate of appropriate length will be prepared, and the roll will be packaged within a substantially water-impermeable, hermetically sealed container such as an aluminum foil plastic laminate pouch. Metal or metal-composite laminates may also be useful. When stored in this manner, uncured casting materials according to the present invention are generally shelf stable for an extended period of time, typically at least one year under a wide range of conditions, such as temperatures of about 0–40° C., and preferably at temperatures of 20–30° C. As used herein, "shelf stable" or "stable" means that the organic oligomers do not react substantially with each other or with themselves to cause an increase in viscosity sufficient to render the material unusable, i.e., having a viscosity over about 500,000 and preferably not over 250 Pa-s, during storage at a temperature of about 0–40° C. Furthermore, when kept from moisture, the compositions remain flowable, flexible, pliable, and capable of adhering to itself or to the desired substrate.

Preparation of a Cured Cast

Cure of the resin-coated sheet of the present invention is accomplished by contacting the curable resin composition with water. In the presence of water the alkoxysilane groups hydrolyze and condense. The resin-coated sheet may be contacted with water by such means as absorption of moisture from the atmosphere, spraying its surface with water, or dipping the resin-coated sheet in water. The rate of cure of the resin-coated sheet can be increased by elevating the water temperature, and thereby increasing the reaction rate and rate of water penetration. In addition, by assuring maximum water contact with all surfaces, the amount of water diffusing into the resin can be increased, resulting in a faster and more complete cure. The use of surfactants and other hydrophilic additives which promote the absorption or diffusion of water into the resin composition can produce a similar effect.

The resin composition can be cured upon exposure to water under a variety of conditions of temperature and pressure. For example, it can cure at a temperature of about 10°–100° C., and preferably about 20°–50° C. Advantageously, however, extreme temperatures are not required. That is, the resin composition of the present invention advantageously can cure at about 20°–40° C. Cure time of the resin-coated sheet can also be decreased by elevating the catalyst concentration and increasing the number of hydrolyzable silane groups.

Orthopedic casting materials, involving the water-curable resin compositions of the present invention are applied to humans or various animals in the same fashion as other known orthopedic casting materials. First, the body part to be immobilized is preferably covered with a conventional cast padding and/or stockinet for protection. Generally, this is a protective sleeve of an air-permeable fabric such that air may pass through the sleeve and the cast to the surface of the skin and moisture vapor may pass out. Preferably, this sleeve does not appreciably absorb water and permits the escape of perspiration. An example of such a substrate is a knitted or woven polypropylene material.

Next, the curable resin is activated, for example, by dipping the orthopedic casting material in water. Excess water is then squeezed out of the orthopedic casting material, and the material is wrapped or otherwise positioned around the body part so as to properly conform thereto. Preferably, the material is then molded and smoothed to form the best fit possible and to properly immobilize the body part in the desired position. Although often not necessary, if desired the orthopedic casting material may be held in place during cure by wrapping an elastic bandage or other securing means around the curing orthopedic casting material. When curing is complete, the body part is properly immobilized within the formed orthopedic cast or splint.

The orthopedic casting material has a working time sufficient to allow the bandage to be positioned and a set time sufficient for the cast to be molded to take the shape of the body part (but short enough that the applier does not waste time). It has a cure time sufficient for the cast to become weight-bearing. The working time is about 1–5 minutes, preferably about 1.5–3 minutes. The set time is about 3–15 minutes, preferably 3–5 minutes. The cure time is about 0.3–24 hours, preferably about 0.3–7 hours and most preferably 0.3–1 hour.

Finally, it is conceivable that some physical characteristics, such as the water resistance, of isocyanate-based casting resins currently on the market could be improved by blending in various proportions of the resins of the present invention.

Other Applications

In addition to orthopedic support materials, the water-curable resin-coated substrates, e.g., sheets, of the present invention can be used for any application where wrapping an object is desirable. For example, such coated substrates can be used to wrap pipes for joining, reinforcement, leak stoppage, protection from abrasion or other abuse, or prevention of escape of insulation fibers such as fiberglass or asbestos. In addition, duct work or other structures that can be wrapped could benefit in a similar manner. Furthermore, such coated substrates can also be used to repair broken or damaged tools such as hoe handles, shovel handles, rake handles, and the like. Sporting equipment can also be reinforced or repaired by wrapping with the present coated substrates. For example, softball and baseball bats and hockey sticks can be wrapped with this material. The coated substrates of the present invention can also be used for patching or bridging gaps to provide a surface for filling and repairs. The resin compositions of the present invention can also be used without a backing as an adhesive, potting compound, sealant, and the like, especially in those applications requiring low viscosity and extended shelf stability.

Test Methods

The following test methods were used to evaluate casting tapes made from the resin composition of the present invention.

Ring Delamination Test

This test measured the force necessary to delaminate a cured cylindrical ring of a resin-coated material within the scope of the present invention. Each cylindrical ring comprised 6 layers of the resin-coated material having an inner diameter of 2 inches (5.08 cm). The width of the ring formed was the same as the width of the resin-coated material employed, namely, 3 inches (7.62 cm). The final calculation of the delamination strength is given in terms of newtons per centimeter of tape width.

Each cylindrical ring was formed by taking a roll of the resin-coated material from its storage pouch and immersing the roll completely in deionized water having a temperature of about 80° F. (27° C.) for about 30 seconds. The roll of resincoated material was then removed from the water and the material was wrapped around a 2 inch (5.08 cm) mandrel covered with a thin stockinet (such as 3M Synthetic Stockinet MS02) to form 6 complete uniform layers using a controlled wrapping tension of about 45 grams per centimeter width of the material. A free tail of about 6 inches (15.24 cm) was kept and the balance of the roll was cut off. Each cylinder was completely wound within 30 seconds after its removal from the water. After 15 to 20 minutes from the initial immersion in water, the cured cylinder was removed from the mandrel, and after 30 minutes (Ring Delamination-30 Minute Test), or 60 minutes, (Ring Delamination-60 Minute Test) from the initial immersion in water, its delamination strength was determined.

This was done by placing the free tail of the cylindrical sample in the jaws of the testing machine, namely, an Instron Model 1122 machine, and by placing a spindle through the hollow core of the cylinder so that the cylinder was allowed to rotate freely about the axis of the spindle. The Instron machine was then activated to pull on the free tail of the sample at a speed of about 127 cm/min. The average force required to delaminate the wrapped layers over the first 33 centimeters of the cylinder was then recorded in terms of force per unit width of sample (newtons/cm). For each material, at least 5 samples were tested, and the average delamination force was then calculated and reported as the "delamination strength."

Ring Compression Tests

In these tests, the "dry strength", "wet strength", and "warm wet strength", of certain cured cylindrical ring samples of the resin-coated materials of the present invention were determined. For each of these tests, cured cylindrical ring samples were formed as described hereinabove with respect to the Delamination Test so as to form 6-layered cylinders around a 2-inch (5.08 cm) mandrel, only all excess material was trimmed off to form these cylindrical rings, leaving no tails.

At a point 30 minutes following the initial immersion in water, each cylinder was removed from its respective mandrel and allowed to cure for 48–60 hours in a controlled atmosphere of 75° F. ±3° F. (34° C. ±2° C.) and 55% ±5% relative humidity. Each cylinder was then placed in a fixture in a commercial testing instrument, e.g., an Instron instrument, and compression loads were applied to the cylindrical ring sample along its exterior and parallel to its axis. The cylindrical ring was placed lengthwise between the two bottom bars of the fixture (the bars being 1.9 cm wide, 1.3 cm in height, and 15.2 cm long), with the bars spaced about 4 cm apart. The inside edges of the bars were machined to form a curved surface having a ⅛ inch (0.31 cm) radius. A third bar (0.63 cm wide, 2.5 cm high, and 15.2 cm long) was then centered over the top of the cylinder, also parallel to its axis. The bottom or contacting edge of the third bar was machined to form a curved surface having a ⅛ inch (0.31 cm) radius. The third bar was brought down to bear against and crush the cylinder at a speed of about 5 cm/min. The maximum or peak force which was applied while crushing the cylinder was then recorded as the ring strength, which in this particular instance is the "dry strength" (expressed in terms of force per unit length of the cylinder, i.e., newtons/cm). For each material, at least 5 samples were tested, and the average peak force applied was then calculated and reported as the "dry strength".

To measure the "wet strength", the same procedure was followed as for the "dry strength", except that after curing for 48–60 hours, the cylinder was then immersed in water at about 113° F. (45° C.) for about 30 minutes, and then allowed to dry at room temperature and pressure for about 15 minutes. The cylinder was then placed in the instrument and crushed as described hereinabove in order to determine the "wet strength" thereof.

To determine the "warm wet strength" of the cylinder, the procedure was followed exactly as set forth for the "wet strength" measurement above, with the exception that the cylinder was placed in the fixture and crushed immediately after removal from the 113° F. (45° C.) water bath and was not allowed to dry at all.

The invention has been described with reference to various specific and preferred embodiments and will be further described by reference to the following detailed examples. It is understood, however, that there are many extensions, variations, and modifications on the basic theme of the present invention beyond that shown in the examples and detailed description, which are within the spirit and scope of the present invention. All starting materials used in the following examples are available from Aldrich Chemical Co. (Milwaukee, Wis.) unless otherwise specified. All percentages and "parts" used herein are based on the total weight of the resin composition, unless otherwise stated. All equivalent weights are given as grams of raw material per equivalent of reactive functionality.

EXAMPLES

Example 1

A sample of 100 grams of Airthane PET-95A (a toluene diisocyanate polyol having 6.23% isocyanate groups, available from Air Products) was mixed with 63.4 grams of bis(trimethoxysilylpropyl)amine (a highly functionalized silane available under the designation A-1170 from Union Carbide) in an eight ounce jar. After shaking the jar by hand for a few minutes, it was placed on a set of rollers of a mixing machine rotating at 16 rpm overnight to insure complete mixing and reaction for 16 hours. The next day 10 grams of this low viscosity material was placed in a 50 ml Tri-Pour (Oxford Labware, St. Louis, Mo.) beaker and 0.2 grams of tetramethylguanidine (TMG obtained from Sigma Chemical Co.) followed by 0.2 grams of dibutyltin dilaurate were added with vigorous stirring, approximately 120 rpms with a ¼" wide metal spatula. After 30 seconds, 4 mL of water was added with gentle stirring. Gelation time was very fast, approximately 20 seconds. The resin hardened in less than 30 minutes and the resulting solid mass obtained after allowing the sample to sit overnight at room temperature was very strong to the touch.

Example 2

The following was mixed under dry nitrogen in a one gallon jar:

| Component: | Equiv. Wt. | Wt % | Grams | Supplier |
|---|---|---|---|---|
| Airthane PET-70D* | 518.50 | 59.04 | 1771.1 | Air Products |
| A-1170 | 341.34 | 37.97 | 1139.0 | Union Carbide |
| Brij ® 58** | 1123.52 | 4.00 | 120.0 | Aldrich |

*A toluene diisocyanate endcapped polytetramethylene oxide with 8.1% isocayanate groups.
**The Brij ® 58 was added as a solid.

The jar was capped and shaken for ten minutes while controlling the exotherm by occasional placement in an ice bath. The jar was placed on a set of rollers for 16 hours, then fitted with an overhead stirrer and nitrogen inlet and heated to 90° C. Next, at 90° C., 62 grams of TMG purchased from Sigma Chemical Co. was added over a 20 minute period with vigorous stirring. Stirring was continued for 1 hour and then the mixture was allowed to come to room temperature. The viscosity of the resin, which was determined on a Brookfield viscometer using spindle no. 6 at 10 rpm, was 89 Pa-s at 23° C. The resin was machine coated on a 3-inch wide (7.62 cm) fiberglass tape of the type described in U.S. Pat. No. 4,609,578 (Reed) at approximately 50% by weight. When immersed in room temperature water and wrapped around a mandrel, the material did not stick to the gloves of the applier. It was slipper, easy to apply, and easy to mold. The physical properties recorded are the average of five samples and gave a standard deviation of less than 3.3 in all cases.

| | AVG. LOAD | |
|---|---|---|
| TEST METHOD | (lbs/inch) | (N/cm) |
| Ring Delamination -- 30 min. | 2.08 | 3.64 |
| Ring Delamination -- 60 min. | 2.51 | 4.40 |
| Ring Compression -- Dry | 48.50 | 84.93 |
| Ring Compression -- Wet | 31.20 | 54.64 |
| Ring Compression -- Warm Wet | 26.60 | 46.58 |

Compared with many conventional casting tapes, the ring delamination numbers are lower than desired; however, the layers stuck together and the strength was good. The dry strength test result is approximately equivalent to that of conventional tapes. The wet and warm wet strengths of this resin system, relative to the dry strength, are significantly better than that of most conventional casting tapes. This indicates a much higher resistance to plasticization by water. Furthermore, a tape containing this resin composition maintains over 50% of its strength in the warm wet test as compared to the dry test, whereas many conventional tapes maintain only about 20% of their strength.

Example 3

A sample of 2,000 grams of Airthane PET-95A was mixed with 979 grams of A-1170 in a one gallon jar under nitrogen. The jar was capped and the contents shaken by hand for 10 minutes while controlling the exotherm with ice water. The jar was then placed on a set of rollers overnight. The next day the jar was fitted with overhead stirrer and nitrogen inlet and heated to 90° C. Next, a 60 gram sample of TMG was added at 90° C. over a 15 minute period and the mixture stirred for 2 hours. After cooling to room temperature the resin was poured in equal portions into 12 separate eight ounce jars under nitrogen. The jars were then capped and eleven of them placed in an oven at 120° F. (49° C.). One jar per week was chosen at random and the viscosity determined on a Brookfield viscometer. The results from this study are as follows:

| WEEK | VISCOSITY (Pa-s) |
|---|---|
| 0 | 53.0 |
| 1 | 54.5 |
| 2 | 62.5 |
| 3 | 63.0 |
| 4 | 64.5 |
| 5 | 67.0 |
| 6 | 69.0 |
| 7 | 70.5 |
| 8 | 70.0 |
| 9 | 75.0 |
| 10 | 78.0 |
| 11 | 79.0 |
| 12 | 72.0 |

Least squares linear regression: slope=2.23 Pa-s/week; r=0.978. The slope of the linear regression (2.23) indicates that the resin composition of the present invention has a rate of viscosity increase less than half that of conventional resins. Preferred materials have viscosities which increase at a rate of less than about 10.0 Pa-s per week, i.e., the slope is less than 10.0 in this test method. This indicates that the aging properties are exceptional. This type of aging study has been proven in the past to correlate well with real life shelf stability of moisture-curable resins impregnated on fiberglass tapes that are stored in moisture-proof pouches for 2–5 years.

Example 4

To a 1 gallon jar was added 2,000 grams of Airthane PET-95A, 9995 grams of A-1170, and 3 grams of Antifoam 1400 (a silicone antifoam available from Dow Corning). The jar was briefly shaken and the exotherm controlled by an ice bath. The mixture was allowed to mix on a set of rollers over the weekend. It was then heated to 75° C. A sample of 61 grams of TMG was then added with vigorous stirring under nitrogen over a 15 minute period. The mixture was stirred for 1 hour. After the mixture came to room temperature, (i.e., about 23° C.), the viscosity was measured on a Brookfield RTV Rotovisco viscometer using spindle no. 6 at 10 rpm and found to be 46,000 cps. The resin was coated on a 3-inch (7.62 cm) wide Scotchcast 2 fiberglass scrim at 46% by weight resin and 4 yard rolls were prepared and placed in sealed pouches. The pouches were placed in an oven at 120° F. (49° C.) for 1 hour and then cooled to room temperature. The following physical property data was collected. The numbers are an average of five runs in most cases with standard deviations less than 2.61.

| TEST METHOD | AVG. LOAD | |
|---|---|---|
| | (lbs/inch) | (N/cm) |
| Ring Delamination -- 30 min. | 1.84 | 3.22 |
| Ring Delamination -- 60 min. | 2.61 | 4.57 |
| Ring Compression -- Dry | 31.60 | 55.34 |
| Ring Compression -- Wet | 20.00 | 11.42 |
| Ring Compression -- Warm Wet | 15.80 | 27.67 |

These results show that a tape with this resin composition maintained 50% of its strength in warm water as compared to its dry strength.

Example 5

The following reagents were mixed in a 1 gallon jar:

| Component: | Equiv. Wt. | Wt % | Grams | Supplier |
|---|---|---|---|---|
| A-1170 | 341.34 | 17.1 | 513.6 | Union Carbide |
| Brij ® 58 | 1123.52 | 4.0 | 120.0 | Aldrich |
| A-1110* | 179.29 | 8.7 | 261.4 | Union Carbide |
| Airthane PET-70D | 688.52 | 69.9 | 2097.1 | Air Products |

*A primary amine (the monofunctional derivative of A-1170).

The jar was shaken briefly by hand and placed on the rollers for 3 hours. After fitting the jar with an overhead stirrer and nitrogen inlet, the mixture was heated to 95° C. A sample of 60 grams of TMG was added over a 10 minute period with vigorous stirring. After 1 hour, the resin was allowed to come to room temperature and then coated on a 3 inch (7.62 cm) fiberglass tape at 45,6% by weight resin. The resulting 4 yard (3.66 m) rolls were placed in moisture-proof packages and placed in an oven at 120° F. (49° C.) for 1 hour. After the rolls came to room temperature, the following physical data were obtained. The numbers are an average of five determinations that gave a standard deviation of less than 1.1 in all cases.

| TEST METHOD | AVG. LOAD | |
|---|---|---|
| | (lbs/inch) | (N/cm) |
| Ring Delamination -- 30 mi | 1.58 | 2.77 |
| Ring Delamination -- 60 min. | 2.10 | 3.68 |
| Ring Compression -- Dry | 20.50 | 35.90 |
| Ring Compression -- Wet | 14.10 | 24.69 |
| Ring Compression -- Warm Wet | 12.30 | 21.54 |

These results show that a combination of silanes is useable in the resin composition of the present invention.

Example 6

The following reagents were mixed in a 1 gallon jar:

| Component: | Equiv. Wt. | Wt % | Grams | Supplier |
|---|---|---|---|---|
| Airthane PET-70D | 518.50 | 59.00 | 1771.1 | Air Products |
| A-1170 | 341.34 | 38.00 | 1134.0 | Union Carbide |
| Brij ® 58 | 1123.52 | 4.00 | 120.0 | Aldrich |

The jar was shaken by hand for 15 minutes while controlling the exotherm with an ice bath. After allowing the mixture to stir on a set of rollers over the weekend, it was heated to 80° C. A sample of 2,750 grams of this material was added to 550 grams of NYAD-G 10012 (a surface treated calcium metasilicate microfiber filter obtained from NYCO Minerals, Inc.) in a separate 1 gallon jar. The resin, with approximately 17% filler content, was placed on the rollers for 2 hours. The temperature was again brought to 80° C. and 66 grams of TMG was added with vigorous stirring while under nitrogen. After stirring for 1 hour, the resin was allowed to come to room temperature and the viscosity was determined to be 110 Pa-s at 23° C. using spindle no. 7 at 10 rpm. This material was coated on a 3-inch (7.62 cm) wide fiberglass tape at 45% by weight of the total resin composition. The following physical data were obtained from freshly prepared rolls. These numbers are the average of five runs and standard deviations were less than 3.1 in all cases.

| TEST METHOD | AVG. LOAD | |
|---|---|---|
| | (lbs/inch) | (N/cm) |
| Ring Delamination -- 30 min. | 0.86 | 1.51 |
| Ring Delamination -- 60 min. | 1.26 | 2.21 |
| Ring Compression -- Dry | 34.20 | 59.89 |
| Ring Compression -- Wet | 19.50 | 34.15 |
| Ring Compression -- Warm Wet | 16.60 | 29.07 |

Although these results show a lesser strength than the resin composition of Example 2, there was less resin used.

Example 7

The following chemicals were mixed in a 16 oz. jar:

| Component: | Equiv. Wt. | Wt % | Grams | Supplier |
|---|---|---|---|---|
| Airthane PET-70D | 518.50 | 60.76 | 121.5 | Air Products |
| A-1170 | 341.34 | 33.11 | 66.2 | Union Carbide |
| Brij ® 58 | 1123.52 | 4.00 | 8.0 | Aldrich |
| TMG | 115.20 | 2.00 | 4.0 | Sigma Chemical |

In this example, the TMG catalyst will be bound to the polymer through reaction of its NH bond with the free isocyanate of the Airthane. The jar was capped and shaken by hand for 5 minutes and the exotherm was cooled by a water bath. After allowing the components to mix on the rollers for 16 hours, 10 grams of the material was placed in a 50 mL Tri-Pour® beaker (Oxford Labware, St. Louis, Miss.) and 4 mL of water added with gentle stirring, approximately 120 rmps with a ¼" wide metal spatula. The resin gelled (i.e., the viscosity was sufficient that when the spatula was dropped through the material, a permanent depression remained) in 5 minutes, became rubbery in 1 hour, and was hard after 3.5 hours. This exemplifies use of a polymer-bound catalyst.

Example 8

To a 500 mL round-bottom flask fired with overhead stirrers, condensors, and nitrogen inlet was added 150 grams of Airthane PPT-95A (a TDI terminated polypropylene glycol obtained from Air Products with a Free NCO of 6.12%) and 41 grams of gamma-mercaptopropyltrimethoxy shane (designated as Y-11167 by Union Carbide). The mixture was heated to 90° C. for 28 hours and then allowed to cool to room temperature. Ten grams of this resin was placed in a 50 mL beaker and 0.2 grams of methanesulfonic acid added with stirring followed by 4 mL of water. The material quickly gelled and cured in about 7 minutes to a rubbery elastomer. This exemplifies a resin of Formula I wherein X=S.

Example 9

The reagents listed below were mixed in a 1 gallon jar:

| Component: | Equiv. Wt. | Wt % | Grams | Supplier |
|---|---|---|---|---|
| Airthane PET-70D | 518.50 | 58.44 | 1869.9 | Air Products |
| A-1170 | 341.34 | 37.78 | 1208.2 | Union Carbide |
| Brij ® 35 | 1199.66 | 4.00 | 128.0 | Aldrich |

The jar was shaken briefly by hand and the exotherm controlled by placement in a cold water bath for 15 minutes. After placing the jar on the rollers of a mixing machine rotating at 16 rpm for 6 hours, 80 grams of TMG were added in small portions over 20 minutes at room temperature while stirring with a highshear mixer available from Premier Mill Corp., Reading, Pa. The jar was then placed on the rollers overnight and the viscosity at 23° C. was measured to be 60 Pa-s. The resin was coated on thirty 48 inch long (122 cm) rolls of 3 inch (7.62 cm) fiberglass tape at 45% by weight resin and the rolls were placed in the 120° F. (40° C) oven for 1 hour. After allowing the rolls to come to room temperature the tape was cured by dipping in 25° C. water, then forming test rolls as described in this test method hereinabove. The following physical testing was done:

| TEST METHOD | AVG. LOAD | |
|---|---|---|
| | (lbs/inch) | (N/cm) |
| Ring Delamination -- 30 min. | 1.50 | 2.63 |
| Ring Delamination -- 60 min. | 2.25 | 3.94 |
| Ring Compression -- Dry | 35.20 | 61.60 |
| Ring Compression -- Wet | 20.30 | 35.50 |
| Ring Compression -- Warm Wet | 15.70 | 27.50 |

These results show that this particularly preferred resin composition had particularly good handling characteristics, e.g., it allowed for an orthopedic casting tape to unwind easily, and of adequate strength.

Example 10

To a 4 oz. jar was added 15 grams of LIIT-240 polyol (purchased from Union Carbide with an equiv. wt. of 237 and now available from Arco) with 14.7 grams of isocyanatopropyltrimethoxy silane (Union Carbide designated as A-1310) and a drop of dibutyltindilaurate (Aldrich). The mixture was placed in a mechanical shaker for 2 hours then on the rollers for an additional 2 hours. Next, 10 grams of this material was placed in a 50 ml Tripour beaker and 0.2 grams of methanesulfonic acid was vigorously mixed into the resin. To this composite was added 5 mL of water and the set time (determined by same method mentioned previously) was 1.5 minutes. The material hardened in less than 2 hours and was brittle and rubbery to the touch.

Example 11

The following was mixed in a 1 gallon jar:

| Component: | Equiv. Wt. | Wt % | Grams | Supplier |
|---|---|---|---|---|
| Airthane PET-70D | 518.5 | 59.0 | 1771.0 | Air Products |
| A-1170 | 341.34 | 38.0 | 1139.0 | Union Carbide |
| Brij ® 58 | 1123.5 | 4.0 | 120.0 | Aldrich |

The jar was shaken briefly by hand and the exotherm controlled by placement in a cold water bath for 15 minutes. After allowing the contents to react for 16 hours on the rollers, 757 grams of NYAD-G filler was added with vigorous stirring via a high shear mixer. The jar was then placed on the rollers for 2 hours after which time 94 grams of TMG was added with vigorous stirring via a high shear mixer. After allowing the resin to mix an additional 16 hours on the rollers, the resin was coated on a polyester knit described in patent application Ser. No. 08/9923 at 77% by weight of the total composite. The following physical data was collected on these samples:

| TEST METHOD | AVG. LOAD | |
|---|---|---|
| | (lbs/inch) | (N/cm) |
| Ring Delamination -- 30 min. | 2.65 | 4.64 |
| Ring Delamination -- 60 min. | 3.35 | 5.87 |
| Ring Compression -- Dry | 41.9 | 73.4 |
| Ring Compression -- Warm Wet | 28.1 | 49.2 |

These results show a relatively strong non fiberglass casting tape can be produced with the resin composition of the present invention.

All patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An orthopedic casting material comprising:
   (a) a water-curable resin composition containing less than about 1 wt-% of a solvent, said resin having a viscosity of no greater than about 500 Pa-s under ambient conditions, said resin composition comprising:
      (i) a water-reactive alkoxysilane terminated prepolymer having at least one hydrolyzable group per molecule; and
      (ii) an effective amount of a catalyst to catalyze the polymerization of said alkoxysilane terminated prepolymer upon contact with water; and
   (b) a porous flexible substrate coated with the water-curable resin composition, wherein said orthopedic casting material is sufficiently porous to enable water to permeate a roll of said casting material during water activation and cause said resin to cure, and wherein said orthopedic casting material is sufficiently porous to allow air and moisture vapor to move through the material after it has been cured.

2. The orthopedic support material of claim 1 wherein the alkoxysilane terminated prepolymer is selected from the group consisting of urethane prepolymers, urea prepolkymers, and prepolymers containing both urea and urethane groups.

3. The orthopedic support material of claim 1 wherein the resin composition contains less than about 0.1 wt-% of a solvent, based on the total weight of the resin composition.

4. The orthopedic support material of claim 1 wherein the resin composition does not significantly increase in viscosity when stored at a temperature of less than about 40° C.

5. The orthopedic support material of claim 1 wherein the catalyst is a basic catalyst.

6. The orthopedic support material of claim 5 wherein the basic catalyst is an amine catalyst.

7. The orthopedic support material of claim 6 wherein the amine catalyst is a substituted guanidine.

8. The orthopedic support material of claim 7 wherein the substituted guanidine is N,N,N',N'-tetramethylguanidine.

9. The orthopedic support material of claim 1 wherein the resin composition is capable of curing upon exposure to water without the generation of substantial heat.

10. The orthopedic support material of claim 1 wherein the water-curable resin composition has a viscosity of about 5–500 Pa-s under ambient conditions.

11. A method of preparing an orthopedic support material comprising coating a porous flexible substrate with a water-curable resin composition containing less than about 1 wt-% of a solvent and having a viscosity of no greater than about 500 Pa-s under ambient conditions, said resin composition comprising:
   (a) a water-reactive alkoxysilane terminated prepolymer having at least one hydrolyzable group per molecule; and
   (b) an effective amount of a catalyst to catalyze the polymerization of said alkoxysilane terminated prepolymer upon contact with water.

12. The method of claim 11 wherein the composition includes about 70–100 wt-% of a water-reactive alkoxysilane terminated prepolymer, based on the total weight of the resin composition.

13. The method of claim 12 wherein the water-reactive alkoxysilane terminated prepolymer is prepared by combining an isocyanate end capped polyol and an alkoxyamino silane.

14. The method of claim 13 wherein the alkoxyamino silane is a secondary amine.

15. The method of claim 13 wherein the isocyanate end capped polyol is prepared from an asymmetric isocyanate.

16. A method of forming an orthopedic cast on a body part comprising:
   (a) covering the body part with a protective sleeve;
   (b) providing an orthopedic casting material comprising a porous flexible substrate coated with a water-curable resin composition containing less than about 1 wt-% of a solvent, said resin having a viscosity of no greater than about 500 Pa-s under ambient conditions, said resin composition comprising:
      (i) a water-reactive alkoxysilane terminated prepolymer having at least one hydrolyzable group per molecule; and
      (ii) an effective amount of a catalyst to catalyze the polymerization of said alkoxysilane terminated prepolymer upon contact with water;
   (c) activating the orthopedic casting material with water; and
   (d) wrapping the body part with the water-activated orthopedic casting material, wherein said orthopedic casting material is sufficiently porous to enable water to permeate a roll of said casting material during water activation and cause said resin to cure, and wherein said orthopedic casting material is sufficiently porous to allow air and moisture vapor to move through the material after it has been cured.

17. A cured orthopedic support prepared from the method of claim 16.

18. A water-curable resin-coated sheet comprising:
   (a) a water-curable resin composition containing less than about 1 wt-% of a solvent and having a viscosity of no greater than about 500 Pa-s under ambient conditions, said resin composition comprising:
      (i) a water-reactive alkoxysilane terminated prepolymer having at least one hydrolyzable group per molecule; and
      (ii) an effective amount of a catalyst to catalyze the polymerization of said alkoxysilane terminated prepolymer upon contact with water; and
   (b) a porous flexible substrate coated with the water-curable resin composition.

19. The water-curable resin-coated sheet of claim 18 wherein the water-reactive alkoxysilane terminated prepolymer is selected from the group consisting of urethane prepolymers, urea prepolymers, and prepolymers containing both urea and urethane groups.

* * * * *

UNITED STATES PATENT AND TRADEMARK OFFICE
CERTIFICATE OF CORRECTION

PATENT NO.: 5,540,652

DATED: July 30, 1996

INVENTOR(S): Andrew J. Callinan and Matthew T. Scholz

It is certified that error appears in the above-identified patent and that said Letters Patent is hereby corrected as shown below:

Col. 4, line 45, "monovaient" should read -- monovalent --.

Col. 4, line 47, "fused-ting" should read -- fused-ring --.

Col. 8, line 54, "$C_3$-$C_{20}$" should read -- $C_3$-$C_{18}$ --.

Col. 9, line 13, "$R^3$ and $R^2$" should read -- $R^2$ and $R^3$ --.

Col. 11, line 15, "Polamine" should read -- Polamine --.

Col. 13, line 34, "acrylonitfile" should read -- acrylonitrile --.

Col. 15, line 24, "yams" should read -- yarns --.

Col. 15, line 28, "yams" should read -- yarns --.

Col. 15, line 40, "yams" should read -- yarns --.

Col. 15, line 49, "apermred" should read -- apertured --.

Col. 17, line 2, "east" should read -- cast --.

Col. 17, line 4, "east" should read -- cast --.

Col. 17, line 25, "pan" should read -- part --.

Col. 17, line 58, "requiting" should read -- requiring --.

UNITED STATES PATENT AND TRADEMARK OFFICE
CERTIFICATE OF CORRECTION

PATENT NO.: 5,540,652
DATED: July 30, 1996
INVENTOR(S): Andrew J. Callinan and Matthew T. Scholz It is certified that error appears in the above-identified patent and that said Letters Patent is hereby corrected as shown below:

Col. 20, line 30, "slipper" should read -- slippery --.

Col. 23, line 33, "Miss." Should read -- Mich. --.

Col. 23, line 34, "rmps" should read -- rpms --.

Col. 23, line 47, "shane" should read -- silane --.

Col. 25, line 28, after "terminated" insert -- nitrogen-containing --.

Col. 26, line 5, after "terminated" insert -- nitrogen-containing --.

Col. 26, line 31, after "terminated" insert -- nitrogen-containing --.

Col. 26, line 53, after "terminated" insert -- nitrogen-containing --.

Signed and Sealed this

Second Day of June, 1998

*Attest:*

BRUCE LEHMAN

*Attesting Officer*    *Commissioner of Patents and Trademarks*